US008668493B2

(12) United States Patent
Janssen et al.

(10) Patent No.: US 8,668,493 B2
(45) Date of Patent: Mar. 11, 2014

(54) LIQUID INTERDENTAL CLEANER

(75) Inventors: Jozef Johannes Maria Janssen, Herten (NL); Bart Gottenbos, Budel (NL); Luciana Opran, Eindhoven (NL); Petrus Henricus Le Leeuw, Someren (NL); Dirk Brokken, Nuenen (NL); Arjan Leo Van Der Sande, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 474 days.

(21) Appl. No.: 12/374,505

(22) PCT Filed: Jul. 6, 2007

(86) PCT No.: PCT/IB2007/052667
§ 371 (c)(1),
(2), (4) Date: Aug. 13, 2009

(87) PCT Pub. No.: WO2008/012707
PCT Pub. Date: Jan. 31, 2008

(65) Prior Publication Data
US 2009/0305187 A1 Dec. 10, 2009

Related U.S. Application Data

(60) Provisional application No. 60/833,091, filed on Jul. 24, 2006.

(51) Int. Cl.
*A61C 3/02* (2006.01)

(52) U.S. Cl.
USPC .............................................. 433/88; 433/216

(58) Field of Classification Search
USPC ............. 433/87–89, 90; 601/166; 137/246.21
See application file for complete search history.

(56) References Cited

U.S. PATENT DOCUMENTS 1,494,809 A    5/1924  Sahr
1,696,486 A    12/1928 Jeffreys
(Continued)

FOREIGN PATENT DOCUMENTS

CH       681597 A5    10/1990
DE       508701 C     10/1930
(Continued)

*Primary Examiner* — Cris L Rodriguez
*Assistant Examiner* — Mirayda A Aponte

(57) ABSTRACT

The interdental cleaner includes a source of liquid (22) and a control system (42) including a manual pump (26), for moving a selected amount of liquid, suitable for a single use, into a liquid pathway and there to a mixing chamber (53). A source of pressurized gas (30), such as a $CO_2$ cartridge, is used to preload a selected amount of gas into a gas chamber (52). The control system includes a spring-loaded button (18), which upon operation results in the manual pump (26) being operated, forcing the selected amount of liquid into the mixing chamber, and then upon release, permits the pressurized gas in the gas chamber to enter the mixing chamber, breaking up the liquid therein into droplets and a liquid stream, and propelling the resulting liquid out of a nozzle portion (14) of the cleaner into the interproximal area of the teeth.

12 Claims, 4 Drawing Sheets

(56) References Cited

U.S. PATENT DOCUMENTS

| | | | |
|---|---|---|---|
| 3,561,433 A * | 2/1971 | Kovach | 601/162 |
| 5,000,684 A | 3/1991 | Odrich | |
| 5,273,428 A | 12/1993 | Fischer | |
| 5,283,924 A | 2/1994 | Kaminski et al. | |
| 5,944,033 A | 8/1999 | Robinson | |
| 6,149,429 A * | 11/2000 | Bukowski et al. | 433/80 |
| 6,253,404 B1 | 7/2001 | Boland et al. | |
| RE38,001 E * | 2/2003 | Adler et al. | 8/142 |
| 6,602,071 B1 * | 8/2003 | Ellion et al. | 433/80 |
| 2004/0014001 A1 | 1/2004 | Nordmo et al. | |
| 2004/0163666 A1 * | 8/2004 | Ochs et al. | 132/323 |
| 2005/0175960 A1 * | 8/2005 | Wiek et al. | 433/88 |
| 2005/0255427 A1 | 11/2005 | Shortt et al. | |
| 2006/0078844 A1 | 4/2006 | Oldman et al. | |
| 2010/0167236 A1 * | 7/2010 | Edwards et al. | 433/89 |

FOREIGN PATENT DOCUMENTS

| | | |
|---|---|---|
| DE | 20013531 U1 | 11/2000 |
| DE | 10145768 A1 | 4/2003 |
| EP | 322223 A2 * | 6/1989 |
| EP | 1064887 A2 | 1/2001 |
| GB | 627654 A | 8/1949 |
| GB | 1317627 A | 5/1973 |
| JP | 2002165806 | 6/2002 |
| WO | 9408533 | 4/1994 |
| WO | 03039392 A1 | 5/2003 |
| WO | 2005030314 A1 | 4/2005 |
| WO | 2005070324 A2 | 8/2005 |
| WO | 2006067760 A | 6/2006 |

* cited by examiner

LIQUID INTERDENTAL CLEANER

TECHNICAL FIELD

This invention relates generally to the field of interdental (interproximal) teeth cleaning devices, and more specifically concerns a system for cleaning interdental areas using a stream of liquid droplets.

BACKGROUND OF THE INVENTION

Dental plaque is normally removed with a toothbrush from those places on the teeth where the toothbrush can reach. In the interdental (interproximal) areas between the teeth, plaque removal is generally more problematic, because the toothbrush bristles cannot physically contact the plaque. In those areas, flossing, toothpicks or certain power toothbrushes are generally recommended to remove the plaque, with the emphasis usually being on flossing.

However, it is well known that flossing can be quite uncomfortable; it can cut the gums, and it may be difficult to manipulate the floss between tightly adjacent teeth, as well as being difficult to maneuver around the mouth. Hence, although flossing has known beneficial results and is recommended by dental professionals, relatively few people floss on a regular basis. Power flossers are known, but are typically based on simulating the mechanical method of flossing or the use of toothpicks and are not widely used.

Accordingly, it is desirable to reach and remove interdental plaque with a system which is effective, yet is also convenient and easy to use.

Accordingly, the present invention is an interdental cleaner, comprising a source of liquid; a system for moving a selected amount of liquid from the source thereof into a liquid pathway; a source of pressurized gas; and a control arrangement for releasing a selected amount of gas into contact with the liquid, resulting in liquid being propelled out of a nozzle portion of the cleaner, to the interdental area of the teeth for cleaning thereof.

BEST MODE FOR CARRYING OUT THE INVENTION

Figure 1:
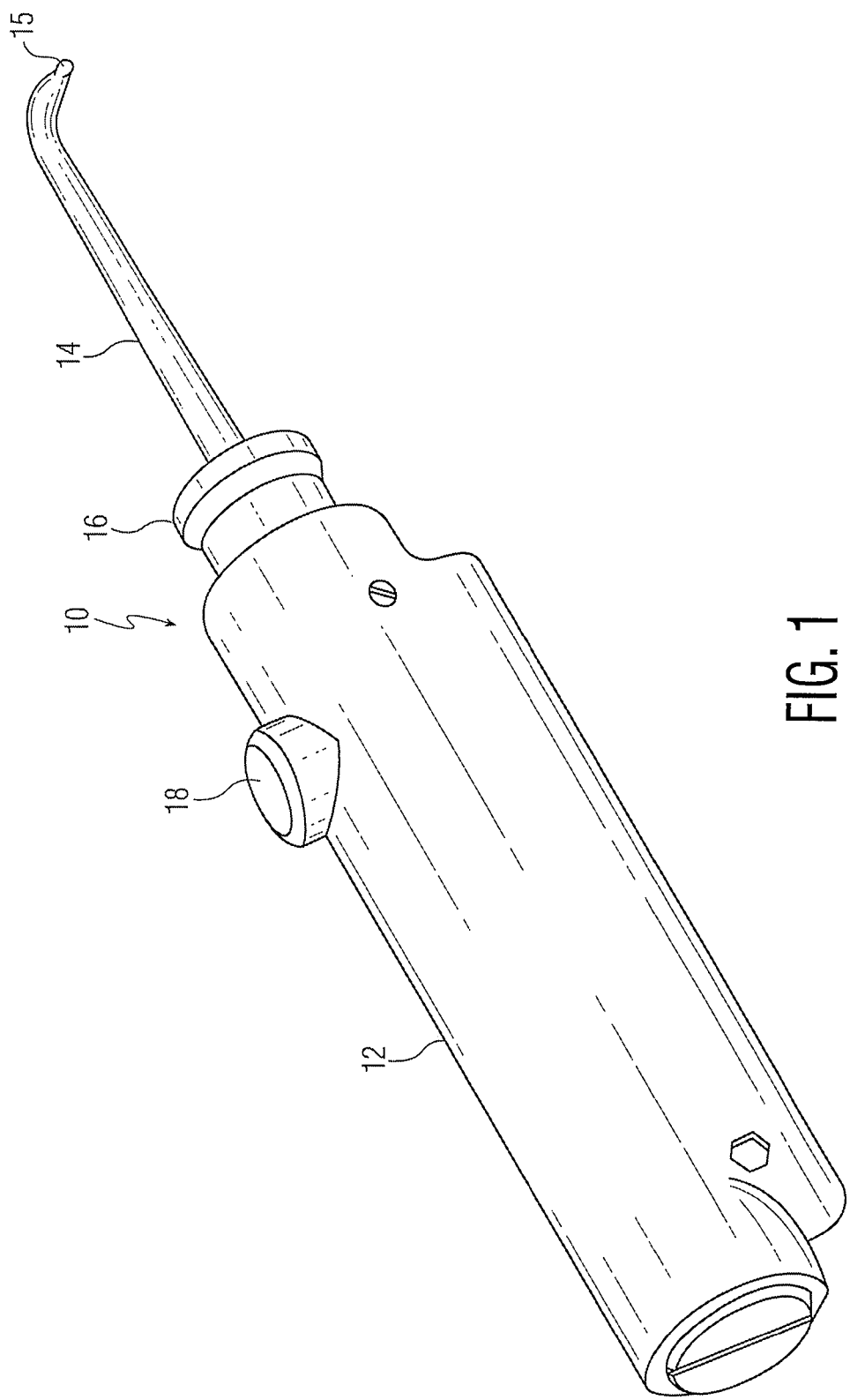
FIG. 1 is a perspective view of the interdental cleaning apparatus of the present invention.
Figure 2:
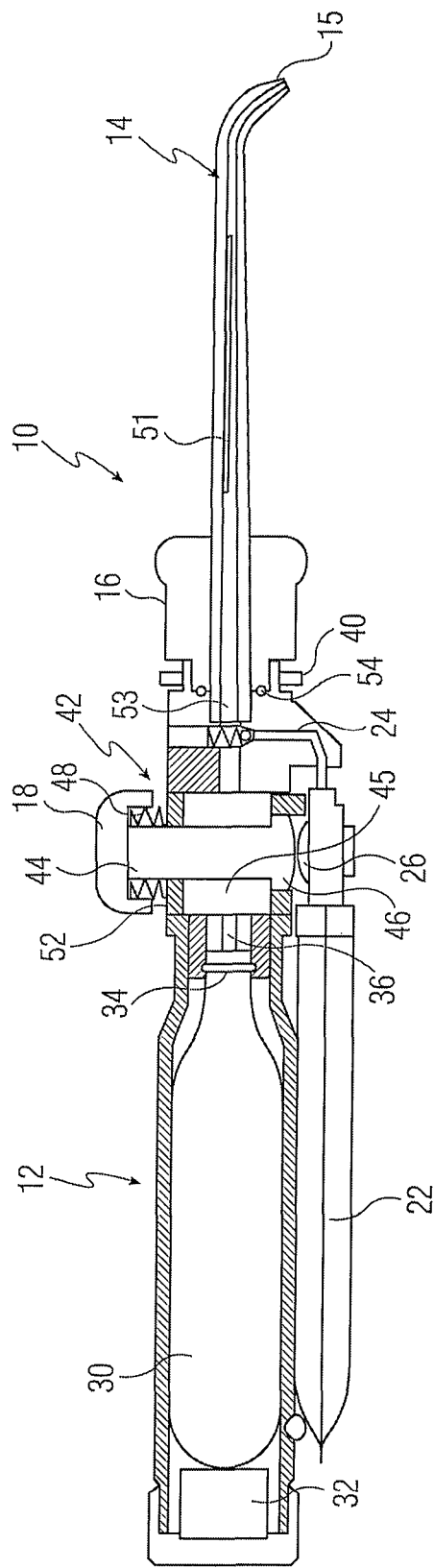
FIG. 2 is a view similar to FIG. 1, showing the internal structure of the interdental cleaning apparatus.
Figure 3A:
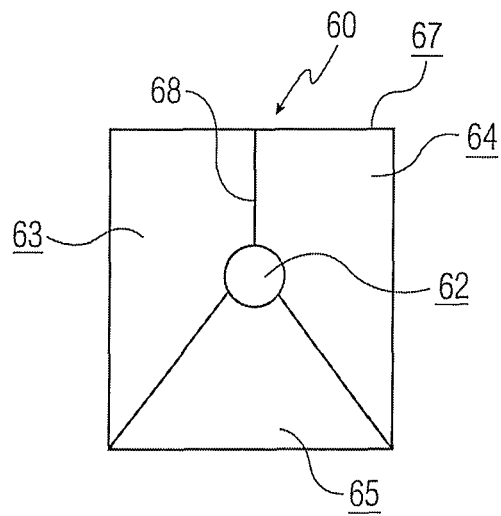
FIG. 3A is a front view of an end portion/nozzle end cap of the interdental cleaning apparatus for guiding the nozzle tip thereof into the interproximal area of the teeth.
Figure 3B:
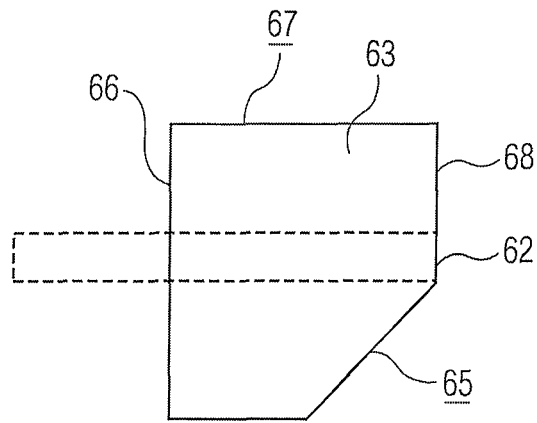
FIG. 3B is a side view of the end portion/nozzle end cap of FIG. 3A.
Figure 3C:
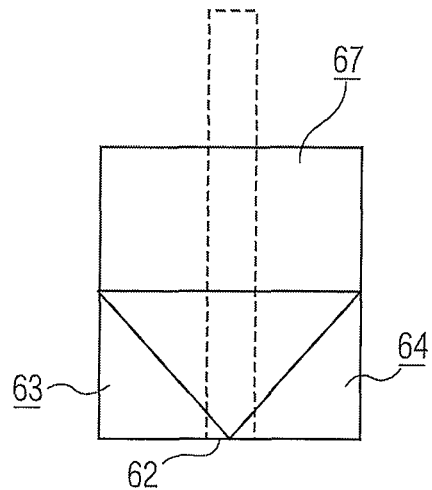
FIG. 3C is a top view of the end portion/nozzle end cap of FIGS. 3A and 3B.

Referring to FIGS. 1 and 2, an interdental cleaning apparatus is shown, generally at 10. The cleaning apparatus includes an exterior housing 12, an extended nozzle member 14 which is hollow along the length thereof, ending at a tip 15, and a nozzle holder 16, in which nozzle member 14 is mounted. The nozzle holder 16 in turn is mounted in housing 12. The operation of the cleaning apparatus 10 is controlled by a control button 18 which, when operated, results in a stream of liquid droplets from the tip end 15 of the nozzle member, at a sufficient velocity, typically in the range of 25-70 msec, preferably with the majority of individual droplets between 40-60 msec, to clean dental plaque from the interdental (interproximal) areas of the teeth. The stream of fluid droplets is produced by directing a small amount of gas into physical contact with a small, predefined amount of liquid, as described in more detail below.

Referring now in more detail to FIG. 2, the apparatus includes a fluid reservoir 22. Typically, the fluid reservoir will contain 10 ml of fluid, although this can vary over a relatively large range, such as up to 40 ml, in a typical hand-held device. The apparatus also includes a small fluid path 24, by which small, predefined amount of liquid are moved from the fluid reservoir to a mixing chamber, at the proximal end of nozzle 14, initiated by operation of a small manual pump 26. In the embodiment shown, the liquid pump capacity is 0.1 ml, although this can also be varied, such as within a preferred range of 0.05-0.5 ml for a single shot. The capacity of the pump is designed to produce a single shot of liquid for a single use, i.e. to clean one interproximal area. The liquid will typically be tap water, but could be other liquids as well, including mouthwash or liquid medications.

The cleaning apparatus 10 also includes a source of pressurized gas 30, which in the embodiment shown is a $CO_2$ cartridge, having a capacity of 12 grams, although this could be in the range of 5-100 grams. The $CO_2$ cartridge 30 is inserted into housing 12 following removal of a base plug 32. When the base plug is inserted, with the $CO_2$ cartridge in place, the top 34 of the $CO_2$ cartridge 30 comes into contact with a hollow needle 36, which punctures the top of the cylinder, permitting escape of the pressurized $CO_2$ gas by a control system/arrangement described in more detail below.

In the embodiment shown, the nozzle member 14 is a hard plastic, approximately 7 mm long, while nozzle holder 16 is also plastic or rubber material. The nozzle holder 16 is rotatably mounted in an end portion of the handle 12 and is held there against the pressure of the gas in the device by a flat aluminum holder member (ring) 40 which secures nozzle holder 16 in place against the high gas pressure within mixing chamber 53.

The apparatus also includes a control assembly 42 which includes control button 18. The control button 18 is mounted with a spring 48 on a shaft 44, at the distal end of which is a disc member 46 which is positioned adjacent fluid pump 26. When the control button 18 is pushed inwardly against spring 48, disc member 46 moves against manual pump 26. As indicated above, the pumped volume is typically approximately 0.1 ml, but could range, preferably between 0.05 0.5 ml, or in some cases up to 5 ml. It is intended to be a single use, i.e. single shot, of liquid for a single interproximal area.

When the $CO_2$ cartridge 30 is punctured by the needle 36 upon loading of the cartridge into housing 12, gas fills a chamber 52. When the button 18 is operated and then released, gas fills the hollow part of member 45. When button 18 is released, a pathway is created from the hollow part of member 45 into the liquid filled mixing chamber 53. The gas pressure is approximately 60 bar, using a liquid $CO_2$ cartridge. The range of pressure could be from 30-200 bar. When the pressurized gas encounters the liquid in the mixing chamber, the liquid mostly breaks up into a plurality of droplets, with some of the liquid remaining in a stream form, and some of the gas remaining in a streaming form, all entering the proximal end nozzle member 14.

The combination of liquid droplets, liquid stream and gas stream proceeds out through the tip 15 of the nozzle 14 to the interproximal areas of the teeth. The presence of the pressurized gas in the mixing chamber 53 produces a significant force on the connection between the handle and the nozzle holder 16. The connection is maintained by a flat aluminum ring 40. A fluid-tight seal between the mixing chamber enclosure and the nozzle holder is maintained by O-ring seal 54. Hence, there is a fluid-tight and pressure-resistant connection between the mixing chamber enclosure at the end of the handle and the nozzle holder 16, which is important to the proper operation of the device.

When the button 18 springs back by action of the spring 48 after it has been released by the user, the device is ready for the next interproximal operation. Typically, each interproximal space will take one liquid burst to be adequately cleaned. In many cases, the device will be used to clean the interproximal spaces from the inside surface of the teeth as well as from the outside surface. This will result in a total of approximately 40 separate bursts of gas-accelerated liquid. If each burst is 0.1 ml, the amount of fluid used per cleaning event in the mouth will be 4 ml.

As indicated above, the nozzle holder 16 is mounted so as to be rotatable and yet remain sealed relative to the fluid chamber enclosure (handle). This enables the device to be used in a wide variety of orientations by a user.

In one particular feature of the invention, a flavored (fresh taste) coating 51 can be added to the inside surface of nozzle member 14. Typically, but not necessarily, it will extend for a significant portion of, and in some cases, the full length of, the nozzle. As the liquid moves through the nozzle, some of the coating material will dissolve in the liquid, providing a desired taste, most particularly a fresh taste, to the user's mouth. The flavors can vary, including, for instance, mint, as well as other flavors, such as cinnamon or lemon. The coating will typically be baked on during manufacture, and will be approximately 5-100 micrometers thick, although this may vary depending upon the particular application.

Another feature, which is shown in FIGS. 3A-3C and 4 are guide mechanisms which are positioned on the tip 15 of the nozzle member 14. In one case, a nozzle end cap 60 (FIGS. 3A-3C) is used which simply fits over the end of the tip 15. The end cap is arranged with an opening 62 at approximately the center thereof through which the spray of liquid is directed. Three angled surfaces 63-65 of the end cap extend downwardly from the opening 62 to a point about half way to the base 66 of the end cap. Rear surface 67 is flat. Two surfaces 63 and 64 mate to define a top line 68. This line 68 fits in the interproximal area, resulting in the droplets being directed to the interdental area. The cap can be made from a soft material so that it conveniently fits between two adjacent teeth.

Figure 4:
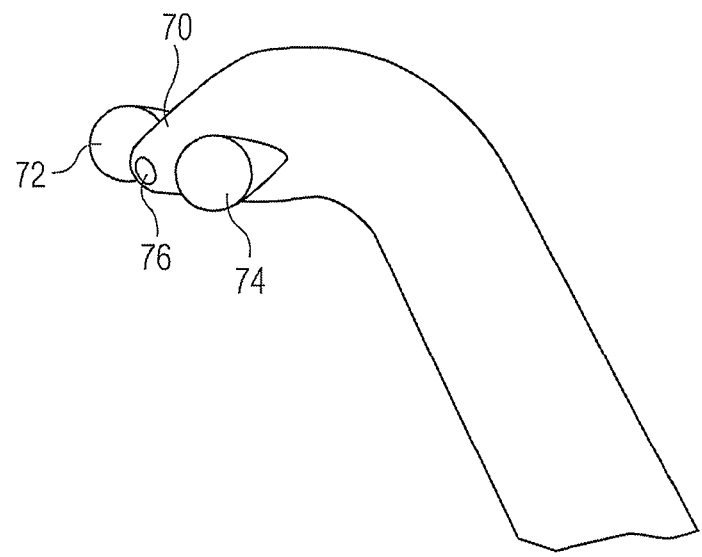
FIG. 4 is a perspective view of another guide member for the nozzle tip of the interdental cleaner of FIGS. 1 and 2.

An alternative is shown in FIG. 4. In this arrangement, near the proximal end 70 of the nozzle are two opposing nodules 72 and 74. These nodules can be made integral with the tip member or can be separate add-on elements. The nodules 72 and 74 can be various configurations, including pointed or spherical, and extend slightly forwardly of or are in the same plane as opening 76 at the tip of the nozzle.

In another operating advantage of the invention, when the device is positioned so that the stream of gas from the nozzle impacts the gum line, the small gas stream will separate the gum from the teeth to a slight extent, such that the liquid droplets can reach the area of the teeth below the gum line, cleaning dental plaque from between the gums and teeth. This is a further function generally accomplished by flossing.

In the embodiment discussed above, the liquid is accelerated by the use of compressed gas from a CO2 cartridge, which produces a stream of liquid droplets. This particular arrangement, besides being effective, has the advantages of relatively low production costs. There is no requirement of an external energy source. In a variation of this arrangement, a small storage tank could be used with a manual pump for compressed air in the hand-held apparatus, eliminating the need for the cartridges of compressed air, but resulting in a larger unit. In another variation, air could be continuously run after the unit has been turned on, with liquid then being injected into the air stream at selected times. An external source of energy would be necessary for this arrangement. In still another variation, a separate small base unit could be used as a source of compressed gas or liquid. The hand-held portion is attached to the base unit, with small chambers for gas and liquid which can be filled from the base unit.

Figure 5:
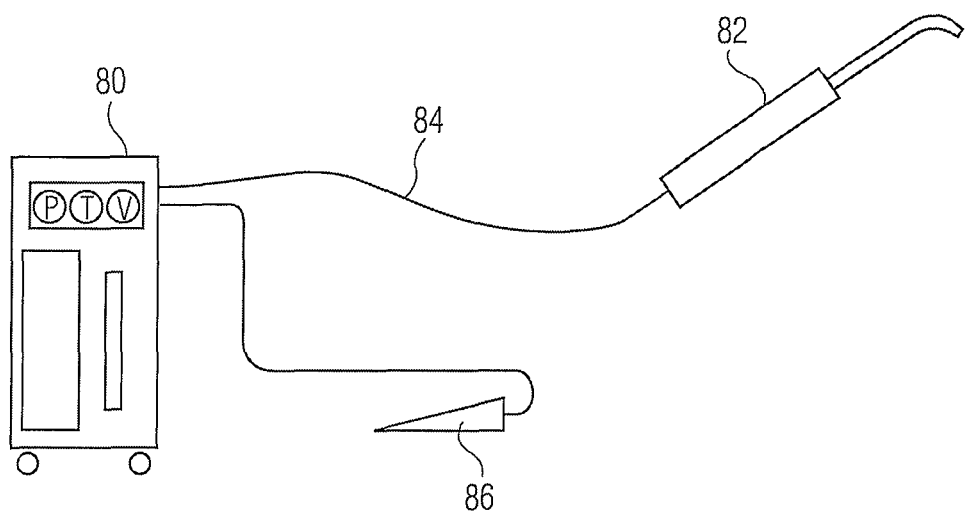
FIG. 5 is a simple schematic view of an interdental cleaning apparatus similar to that of FIGS. 1 and 2 and suitable for use in a dental office.

In a further development, for use in a dental office for instance, shown in FIG. 5, a separate, large base unit 80 can be used as a source of both liquid and compressed gas. The hand unit 82 is connected to the base unit via a tether 84. The hand unit can be operated with a foot pedal 86. An advantage of this arrangement is that the unit can be used without reloading for a long period of time.

As a further variation or feature, all of the above embodiments can be used with bristles, providing a scrubbing action in addition to the inter-dental cleaning. The action can be used for both manual and power bristle arrangements.

Accordingly, an interdental cleaner has been disclosed which is arranged to provide a stream of liquid under fairly high pressure, at velocities of approximately 25-70 meters per second from the tip, which stream of liquid droplets can be directed toward the interproximal area of the teeth to clean dental plaque therefrom. This arrangement is not only effective, but it is convenient and easy to use, and will provide reliable interproximal cleaning without the inconvenience and discomfort of flossing.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. An interdental cleaner, comprising:
   a source of liquid (22);
   a source of pressurized gas (30) and an associated gas chamber (52) into which gas is released; and
   a control arrangement (18, 42, 44, 46, 26) which includes a spring-loaded movable member (18) which (1) upon operation moves a selected amount of liquid from the source thereof to a mixing chamber (53) by pump action, and (2) upon release of the spring-loaded movable member a selected amount of gas present in the gas chamber is allowed to move into the mixing chamber into contact with the liquid therein, resulting in liquid, which includes liquid droplets being propelled out of a nozzle portion (14) of the cleaner, to the interdental area of the teeth for cleaning thereof.

2. The interdental cleaner of claim 1, wherein the selected amount of liquid is within the range of 0.05-0.5 ml for a single use.

3. The interdental cleaner of claim 1, wherein the liquid is primarily in the form of droplets when it leaves the nozzle portion.

4. The interdental cleaner of claim 1, wherein the source of pressurized gas is a $CO_2$ cartridge.

5. The interdental cleaner of claim 1, wherein the gas is under pressure of approximately 60 bar, and wherein the velocity of the liquid droplets upon leaving the nozzle is within the range of 25-70 meters per second.

6. The interdental cleaner of claim 1, wherein the liquid leaving the nozzle is both in the form of droplets and a liquid stream, accompanied by an amount of gas in a stream.

7. The interdental cleaner of claim 1, including a flavored coating (51) on the inside of the nozzle, which partially dissolves upon contact with the liquid as it moves through the nozzle, providing a desired taste to the user during contact of the liquid with the teeth of the user.

8. The interdental cleaner of claim 1, wherein the nozzle is mounted in a nozzle holder (16) and the apparatus includes sealing member (54) between the nozzle holder and handle portion (12) of the cleaner, arranged to permit the nozzle holder and the nozzle to be rotatable relative to the handle.

9. The interdental cleaner of claim 1, including a guide member (60,72,74) on the distal end of the nozzle member, configured to provide guidance for locating the nozzle relative to the teeth, so that the stream of liquid droplets from the nozzle is directed toward the interproximal areas of the teeth.

10. The interdental cleaner of claim 9, wherein the guide member includes two separate nodules (72,74) located on opposing sides of a tip end of the nozzle member, the two modules being approximately coplanar or slightly forward of a liquid exit opening in the tip end of the nozzle member.

11. The interdental cleaner of claim 1, wherein the source of liquid and the source of pressurized gas are located in a unit (80) separate from the remainder of the interdental cleaner.

12. The interdental cleaner of claim 1, wherein the selected amount of gas is provided continuously after the cleaner is turned on, and liquid is injected periodically into the stream of gas, resulting in a stream of liquid droplets.

* * * * *